United States Patent [19]

Bunnell

[11] Patent Number: 4,481,944
[45] Date of Patent: Nov. 13, 1984

[54] APPARATUS AND METHOD FOR ASSISTING RESPIRATION

[75] Inventor: J. Bert Bunnell, Salt Lake City, Utah

[73] Assignee: Bunnell Life Systems, Inc., Salt Lake City, Utah

[21] Appl. No.: 322,742

[22] Filed: Nov. 19, 1981

[51] Int. Cl.³ .............................................. A61B 7/00
[52] U.S. Cl. ............................................. 128/204.18
[58] Field of Search .................. 128/203.14, 203.16, 128/203.17, 203.22, 203.26, 203.27, 204.17, 204.18, 204.21, 204.23, 204.25, 204.26, 205.15, 207.14

[56] References Cited

U.S. PATENT DOCUMENTS

| 2,302,023 | 11/1942 | Glasser | 128/204.17 |
| 3,191,596 | 6/1955 | Bird et al. | 128/204.26 |
| 3,523,527 | 8/1970 | Foster | 128/204.21 |
| 4,016,878 | 4/1977 | Castel et al. | 128/203.26 |
| 4,155,356 | 5/1979 | Venegas | 128/207.14 |
| 4,211,221 | 7/1980 | Schwanbom et al. | 128/204.18 |
| 4,351,329 | 9/1982 | Ellestad et al. | 128/204.21 |

Primary Examiner—William E. Kamm
Attorney, Agent, or Firm—Thorpe, North & Western

[57] ABSTRACT

Apparatus and method for assisting a person's respiration by means of application of a series of high pressure air pulses to the person. The frequency of the pulses is varied over some range of frequencies to ensure that at least during some portion of the time, air pulses are applied to the person at the natural or resonant frequency of the person's respiratory system.

30 Claims, 4 Drawing Figures

APPARATUS AND METHOD FOR ASSISTING RESPIRATION

BACKGROUND OF THE INVENTION

This invention relates to a new and improved method and apparatus of assisting ventilation and respiration of a person.

It has been found that persons with various respiratory problems and illnesses can be benefitted by application to the person's respiratory system of rapid, positive pressure pulses of oxygen and air. This type of "ventilation" is superior to the more conventional method of ventilation which consisted of application of relatively large volumes of oxygen and air to a person at frequencies which coincided substantially with the inhalation frequency of the person. Some of the problems with this conventional technique are that those areas of the lung with the least blood perfusion may be preferentially ventilated, added resistance to blood flow into the thorax and pulmonary capillaries is imposed, and blood pressure is oftentimes altered. In addition, the decreased compliance of the lungs of those persons who suffer from respiratory distress syndrome causes high intrapulmonary pressures to be necessary during the application of the oxygen-air pulses. These high pressures oftentimes produce the side affects of pneumothorax, cerebral hemorrhage and broncho-pulmonary dysplasia, all of which are life threatening and debilitating.

Two prior art methods of applying positive pressure pulses of gas to a patient at a higher than normal rate of inhalation and exhalation are disclosed in U.S. Pat. Nos. 4,155,356 and 2,918,917. In the first mentioned patent, '356, the object of the method described is to alleviate respiratory problems caused from a collapsed lung passageway which, for example, may result from emphysema. The apparatus and method of the '356 patent provide for supplying a series of pressure pulses to the air passageway in question, with the pulses having a certain defined wave form and frequency rate. Further, the person on which the method is used is generally able to inhale but not exhale and so the method is used to assist exhalation only. Thus, the '356 patent is not directed strictly to assisting respiration—both inhalation and exhalation—to alleviate respiratory problems.

The '917 patent discloses apparatus for "vibrating portions of a patient's airway" at a rate which is greater than the patient's normal rate of inhalation and exhalation. The purpose of this is to exercise and massage the airway and associated organs to thus loosen and remove mucous therefrom. It was also stated in the patent that it was believed that vibrating portions of a patient's airway aided in the breathing function by circulating the gas more thoroughly to and from the walls of the lungs.

Although the application of high frequency, positive pressure pulses of gas to a person's respiratory system provides benefits not achievable with the conventional method of ventilation, the optimum use of high frequency, positive pressure pulses has not yet been achieved.

SUMMARY OF THE INVENTION

It is an object of the invention to provide a new and improved method and apparatus for applying high frequency, positive pressure pulses of gas to a person's respiratory system to assist breathing and ventilation.

It is another object of the invention to provide such method and apparatus whereby the pulses of gas may be applied to the person at or near the natural or resonant frequency of the person's respiratory system.

It is still another object of the invention to maximize ventilation and respiration in a person while minimizing positive pressure and oxygen concentration of gas pulses applied to the person.

It is an additional object of the invention to periodically apply pulses of gas to a person at frequencies which correspond to the various natural or resonant frequencies of the different parts of a person's respiratory system.

The above and other objects of the invention are realized in an illustrative method and apparatus by which a series of gas pressure pulses are produced and applied to a person's respiratory system, and the frequency of the pulses are varied over some range of frequencies which is broad enough to encompass the natural or resonant frequency of the person's respiratory system. By applying the pulses to the person at or near the natural frequency of the person's respiratory system, less resistance is encountered in suffusing the lungs with the gas thereby reducing the gas pulse pressure required to ventilate the lungs.

BRIEF DESCRIPTION OF THE DRAWINGS

The above and other objects and advantages of the invention will become apparent from a consideration of the following detailed description presented in connection with the accompanying drawings in which.

DETAILED DESCRIPTION

Figure 1:
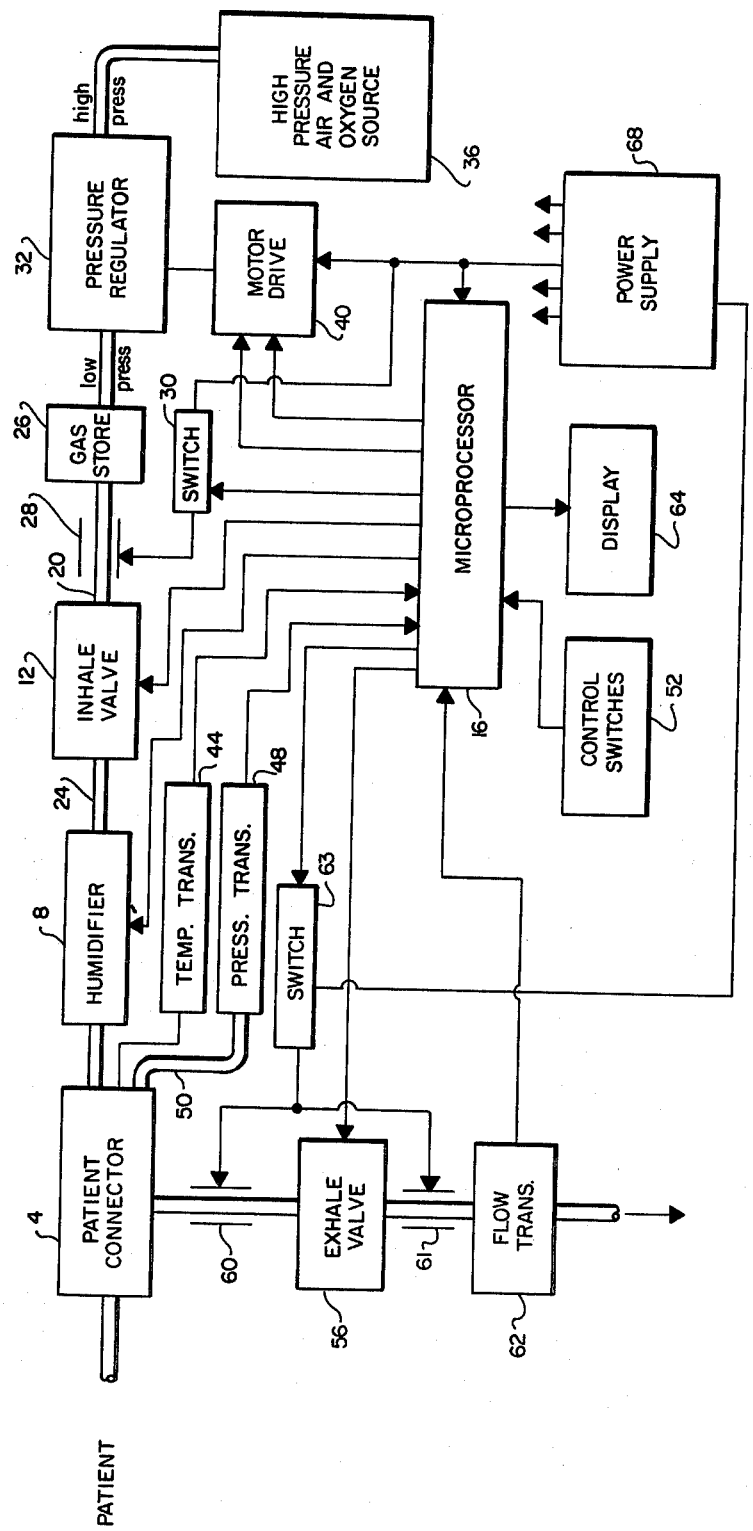
FIG. 1 shows a schematic of apparatus for assisting a person's respiration constructed in accordance with the principles of the present invention.
Figure 2:
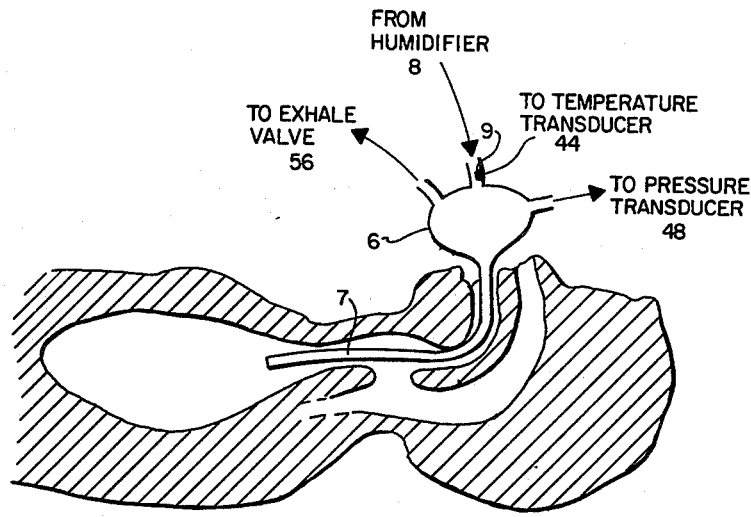
FIG. 2 shows one illustrative arrangement for coupling the apparatus of FIG. 1 to a person's respiratory system.

FIG. 1 shows a schematic of a system for applying a series of high pressure gas pulses to a patient's respiratory system. The system is coupled to the patient by a patient connector 4 which may take the embodiment shown in FIG. 2. In this embodiment, a manifold 6 interconnects tubes from various elements of the system with a tube 7 which is inserted into the patient's mouth (or nose) and throat as shown. Also shown in FIG. 2 is a probe 9 placed in a tube which brings humidified gas to the manifold 6. The probe 9 is provided for detecting the temperature of the gas just before it reaches the patient. It should be understood that there are a variety of ways in which the gas pulses could be applied to a patient, and the particular arrangement shown in FIG. 2 is just one illustrative way.

Gas pressure pulses are received by the patient connector 4 from a humidifier 8 which is adapted to supply moisture to the pulses of gas. The humidifier may be any conventional type of humidifier such as Model 3000 produced by Bird Corporation.

The gas pulses are produced by operation of an inhale valve 12 which alternately opens and closes in response to signals received from a microprocessor 16. The inhale valve 12 is simply operated to open and close at some frequency to thereby allow gas to flow from an input conduit 20 to an output conduit 24 leading to the humidifier 8. In particular, the microprocessor 16 alternately applies open and close signals to the inhale valve 12 to cause it to respectively open, to allow passage of gas, and close, to prevent the passage of gas. When this is done at a fairly high frequency, gas pressure pulses are produced in the outlet conduit 24 for ultimate supply via the patient connector 4 to a patient. The inhale valve 12 may be a conventional fluid control valve such as Model C-20 produced by Precision Dynamics, Inc. The microprocessor 16 could advantageously be a Motorola 6801 which is programmable to produce a variety of signals as desired by the user and to produce a variety of other output signals in response to various input signals. This will be discussed more hereafter.

Gas is supplied to the inhale valve 12 via conduit 20 from a gas storage tank 26. The gas storage tank receives gas under low pressure and then temporarily stores it for ultimate supply to the inhale valve 12. The gas storage tank serves to maintain a substantially constant flow of gas under a substantially constant pressure to the inhale valve. In effect the gas storage unit 26 acts as a buffer or as a capacitor would in an electrical circuit.

Disposed between the inhale valve 12 and the gas storage unit 26 is a heater 28 which serves to heat the gas or air supplied by the gas storage unit to the inhale valve. The specific function of this heater will be described later. The heater could simply be a coil of electrically resistive wire positioned about the conduit 20 and designed to produce heat when electrical current is supplied thereto via a switch 30 from a power supply 68. Alternatively, the gas or air could be heated in the humidifier 8 by some type of conventional heater.

The gas supplied to the gas storage unit 26 is received from a pressure regulator 32 which reduces the pressure of the gas from the pressure at which the regulator receives the gas from an air and oxygen source 36. Such a source could be a conventional air or gas storage tank and the pressure regulator 32 is a conventional regulator for regulating pressure of gas passing therethrough. The pressure of the gas supplied to the air storage unit 26 may be varied by the pressure regulator 32 in response to operation of a motor drive unit 40 which, in turn, is controlled by the microprocessor 16.

Also included as part of the input portion of the system of FIG. 1 are a temperature transducer 44 and a pressure transducer 48 coupled to the patient connector 4. The temperature transducer simply senses the temperature of the gas being delivered to the patient in response to a temperature signal received from the probe 9 (FIG. 2). The pressure transducer 48 measures the air or gas pressure at the mouth of the patient and is interconnected by a tube 50 to the patient connector 4 (e.g. manifold 6 of FIG. 2). Alternatively, the pressure transducer may be connected via a separate tube to other locations such as the distal end of the tube 7 inserted into the mouth and throat of the patient. An exemplary temperature transducer is that produced by Yellow Springs Instrument Co., Inc., and identified as series 400, and an exemplary pressure transducer is Validyne Engineering Sales Corp., model DP 45.

Signals from the temperature transducer and pressure transducer, indicating respectively the temperature and pressure of the gas being supplied to the patient, are provided to the microprocessor 16 which then supplies appropriate signals to the heater 28 and to the motor drive unit 40 to control the temperature and pressure. In particular, it is desired that the gas pulses be supplied to the patient so as not to cool the patient, and for this reason a heater 28 is provided to maintain the gas pulses at a temperature which will maintain the temperature of the patient at the normal body temperature. Thus, if the temperature transducer indicates that the patient's temperature may fall below the normal body temperature as a result of the gas being delivered to his lungs, the microprocessor 16 would signal the switch 30 to allow more current to flow from the power supply 68 to the heater 28 to increase the heat produced and thus increase the temperature of the gas pulses supplied to the inhale valve 12. The switch 30 might illustratively be a Teledyne solid-state relay no. 601-1003.

Likewise, the pressure measurement determined by the pressure transducer 48 is supplied to the microprocessor 16 so that the microprocessor can signal the motor drive unit 40 which in turn controls the pressure regulator 32 to supply gas to the gas storage unit 24 at a certain desired pressure. A certain pressure level is generally necessary to properly ventilate a patient but it is desired that this pressure be minimized to the extent possible while still providing adequate ventilation for the patient. The pressure regulator 32 would typically reduce the pressure from about 50 pounds per square inch to about 2 to 30 pounds per square inch. The microprocessor 16 in response to signals from the pressure transducer 48 controls the output pressure of the pressure regulator 32 to maintain it at some preselected pressure. Such preselected pressure level could be pre-programmed into the microprocessor via control switches 52.

The humidifier 8 is provided to humidify the gas pulses supplied to the patient to avoid dehydrating the patient's pulmonary mucous membranes.

Also coupled to the patient connector 4 is an exhale valve 56 which operates 180 degrees out of phase with the inhale valve 12 so that when the inhale valve is opened the exhale valve is closed, and when the inhale valve is closed, the exhale valve is opened. The exhale valve 56 operates under control of the microprocessor 16 and in response to signals supplied thereby to alternately open and close. The purpose of the exhale valve 56 being closed when the inhale valve is open is to ensure that the pulses reach the patient via the patient connector 4 and are not simply routed to and through the exhale valve. Of course the exhale valve 56 is opened periodically to allow release of exhaled gas from the patient to the atmosphere.

Heaters 60 and 61 are provided to warm the gas flowing from the patient connector 4 to the exhale valve 16 and from the exhale valve to a flow transducer 62 to prevent condensation which might otherwise endanger the patient by flowing back into his lungs, or tend to foul up the flow transducer 62 (to be discussed momentarily). The heaters 60 and 61 operate to produce heat from current supplied via switch 63 from a power supply 68. The switch 63 controls the amount of current supplied to the heaters 60 and 61 in response to signals from the microprocessor 16.

The flow transducer 62 provides a signal to the microprocessor 16 indicating the volume of gas per unit time delivered to the patient. This information is utilized to calculate the volume of each exhaled breath and the volume of gas that the patient is exhaling per minute. It is also used in the measurement of quasi-static lung compliance which will be discussed momentarily.

A display unit 64 is coupled to the microprocessor 16 to display various parameters associated with the system and a power supply unit 68 is provided to supply power to the microprocessor, motor drive, and other elements in the system.

The method of the present invention contemplates varying the frequency of the gas pulses supplied to the patient over some range of frequencies. The range of frequencies over which the gas pulses would be varied is selected to ensure that the natural or resonant frequency of a patient's respiratory system falls within that range. It has been found that a person's respiratory system has a natural or resonant frequency and that various parts of the respiratory system also have their own natural frequencies. See, for example, Dubois, A. B., Brady, A. W., Lewis, D. H., and Burgess, B. F., "Oscillation Mechanics of Lungs and Chest in Man", *Jour. of App. Physiology*, 8, 587 (1956) and Peslin, R., "Theoretical Analysis of Airway Resistances on an Inhomogeneous Lung", *Jour. of App. Physiology*, 24, 761 (1968). By sweeping over a range of frequencies, such as from 2 to 30 Hertz, the gas pulses will be supplied to the patient at the natural frequency of the patient's respiratory system at least some of the time, and also at the natural frequencies of various subparts of the respiratory system at least some of the time. Advantageously, the natural frequency of a person's respiratory system would be determined before treatment (for example by using the method described in Williams, S. P., Fullton, J. M., Tsai, M. J., Pimmel, R. L., and Collier, A. M., "Respiratory Impedance and Derived Parameters in Young Children by Forced Random Noise", *Jour. of App. Physiology: Respiratory, Environmental and Exercise Physiology*, 47(1), 167 [1979]) and then the range of frequencies would be centered about this natural frequency to sweep, for example, between 5 to 10 Hertz below the natural frequency and 5 to 10 Hertz above the natural frequency. By supplying gas pulses to a person's respiratory system at or near the system's natural frequency, less reactance is encountered, and thus a lower positive pressure may be used to provide the gas pulses. Also, better ventilation of the respiratory system is achieved when the pulses are supplied at or near the natural frequency.

To provide the sweep of frequencies of the gas pressure pulses, the microprocessor 16 is simply programmed to vary the frequency of application of the open and close signals supplied to the inhale valve 12 and exhale valve 56. That is, the frequency of application of the open and close signals determines the frequency of the gas pressure pulses. Thus, simply by varying this frequency over some range, the frequency of the gas pulses are likewise varied. Of course, the range of the frequency sweep can be manually selected by control switches 52.

To measure static lung compliance (which is a measure of elastic recoil of lungs—see Freeman, C., Cicerchia, E., Demers, R. R., and Saklad, M., "Static Compliance, Static Effective Compliance, and Dynamic Compliance as indicators of Elastic Recoil in the Presence of Lung Disease", *Respiratory Care*), control switches 52 are manually operated to cause interruption of normal operation of the system. Then, the patient's lungs are inflated by gas supplied via regulator 32, store 26, etc. to a moderate pressure of approximately 25 cm $H_2O$ and held in that static condition for approximately one second. The exact pressure at the end of that static period, $P_s$, is measured by the pressure transducer 48.

The patient is then allowed to exhale through the exhale valve 56 and flow transducer 62. The flow transducer 62 measures the exhaled gas flow and the microprocessor 16 integrates that measurement over the time allowed for complete exhalation thus producing a measurement of exhaled volume. The exhaled volume, $V_t$, is then divided by the value $P_s$ to produce the calculated static overall compliance, C: $C=(V_t/P_s)$. This valve, C, is then displayed on the front panel display 64.

Figure 4:
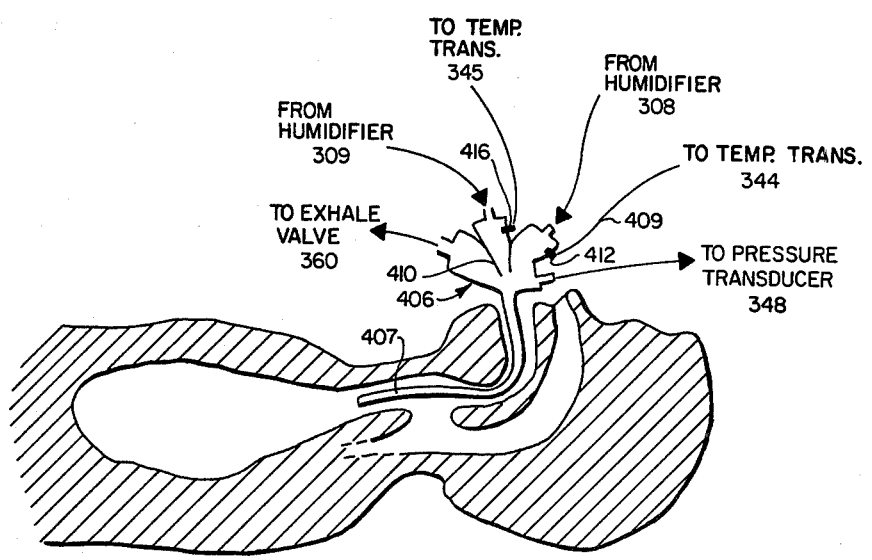
FIG. 4 shows coupling apparatus for use with the embodiment of FIG. 3.
Figure 3:
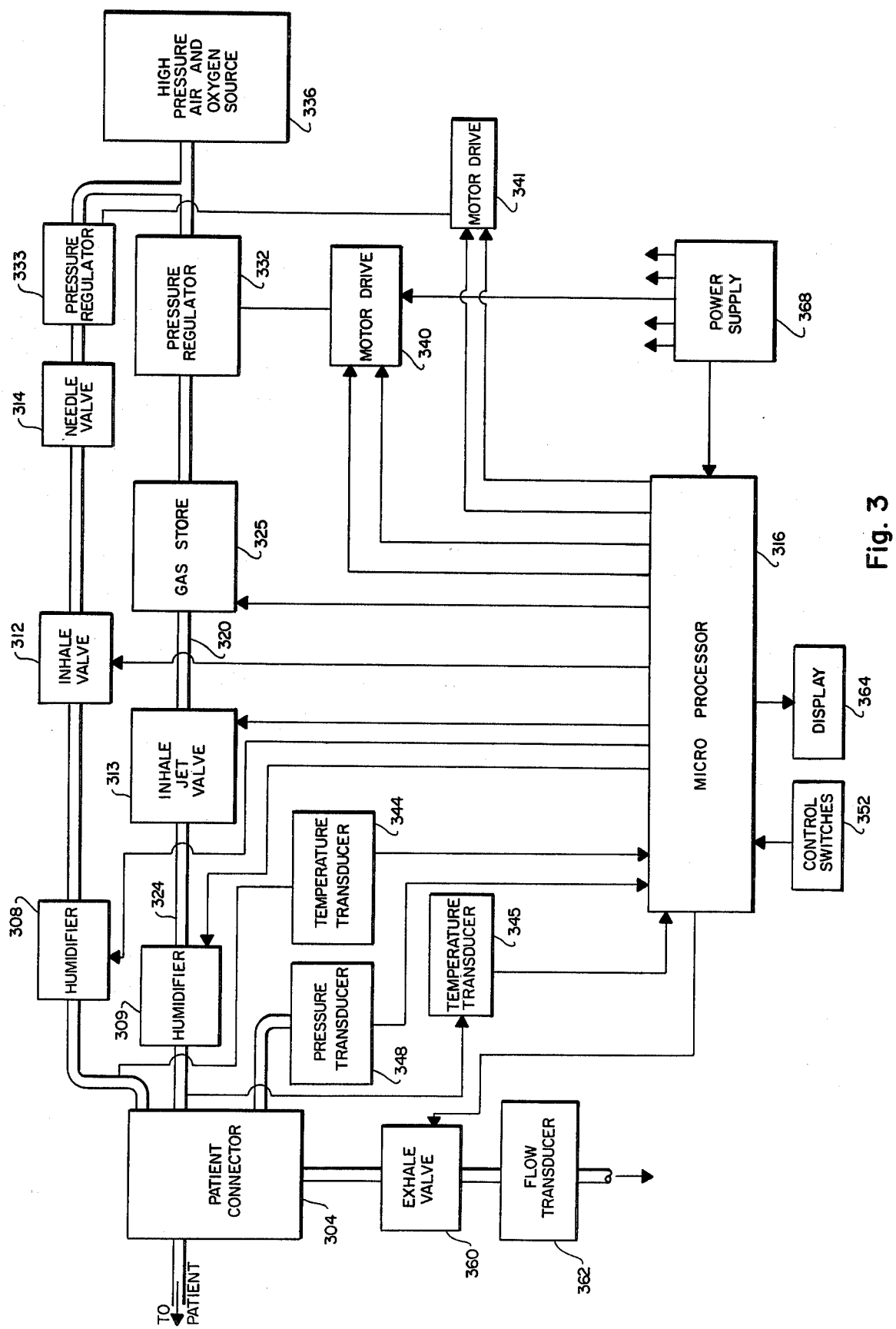
FIG. 3 shows a schematic of an alternative embodiment of apparatus for assisting a person's respiration.

FIG. 3 shows a schematic of an alternative embodiment of a system for applying gas pulses to a patient's respiratory system. The system of FIG. 3 is coupled to a patient by way of a patient connector 304, an illustrative embodiment of which is shown in FIG. 4. Referring to FIG. 4, there is shown manifold 406 which interconnects various elements of the system of FIG. 3 with a tube 407 which is inserted into the patient's mouth (or nose) and throat as shown. The manifold 406 of FIG. 4 differs from the manifold 6 of FIG. 2 in that the former includes an inlet jet nozzle 410 for receiving gas pulses from a second humidifier 309 as will be discussed momentarily. The jet nozzle 410 projects within the manifold 406 to a point near the proximal end or into the lumen of the tube 407 and may, for example, be comprised of a 14 gauge hypodermic needle.

Probes 412 and 416 are disposed in the wall of the manifold 406 to respectively detect the temperature of gas being supplied by the humidifier 308 and humidifier 309. Signals from the probes 412 and 416 are supplied respectively to temperature transducers 344 and 345 (FIG. 3) which, in turn, supply signals to a microprocessor 316 to indicate the desired temperatures. If the temperatures are below certain predetermined levels, then the microprocessor 316 signals heaters located in humidifiers 308 and 309 to increase their heating as needed to raise the temperatures to the predetermined levels established for the humidifier 308 and humidifier 309. This, of course, is similar to the FIG. 1 system except that temperature is measured and gas heated at two different locations in the FIG. 3 system. The humidifiers 308 and 309 humidify the gas being supplied to the patient.

The difference between the FIG. 3 system and the FIG. 1 system is that the FIG. 3 system includes two paths by which gas is supplied to the patient. One path includes humidifier 308, inhale valve 312, a needle valve 314 and a pressure regulator 333 connected to a high pressure air and oxygen source 336. Gas pulses are supplied via this path at or near a normal breathing rate, e.g. from about 10 to 30 pulses per minute. (For infants, it may be desirable to pulse up to 100 pulses per minute.) Rates less than 10 per minute would be used when the patient can successfully breathe on his own for most of the time. This is done by supplying gas under high pressure from the source 336 to the pressure regulator 333 which reduces the pressure to about 5 to 15 psig. The gas is then supplied to the needle valve 314 which determines the volume of gas flowing in this path. Advantageously, the needle valve 314 is set to allow a volume flow of from 10 to 40 liters per minute. From the needle valve, the gas flows to the inhale valve 312 which is alternately opened and closed by the microprocessor 316 at a rate corresponding generally to the normal breathing rate of the patient. When the inhale valve 312 is opened, an exhale valve 360 is closed and vice-versa, to thereby force gas via the humidifier 308 and patient connector 304 into the patient's endotracheal tube.

Alternately, inhale valve 312 may remain open continuously while exhale valve 360 is alternately closed and opened thereby forcing gas from humidifier 308, etc. into the patient or inhalation and allowing for passive exhalation respectively. This technique also allows the patient to breath spontaneously during those periods when both the inhale and exhale valves, 312 and 360 respectively, are open.

The other path by which gas is supplied to the patient includes the humidifier 309, an inhale jet valve 313, a gas storage unit 325, and a pressure regulator 332 connected to the high pressure air and oxygen source 336. Through this path, gas is supplied in pulses at high frequency which varies over some predetermined range. The gas flows from the high pressure source 336 to the pressure regulator 332, which reduces the pressure of the gas, and from there to to a gas storage unit 325. The gas storage unit 325 performs the same function as the gas storage unit 26 of FIG. 1. From the gas storage unit 325, the gas is supplied to the jet valve 313, which is controlled by the microprocessor 316 to open and close at a frequency which varies over a predetermined range such as from about 2 Hertz to 40 Hertz. The jet valve 313 may be a conventional fluid control valve such as model c-20 produced by Precision Dynamics, Inc. The gas then flows via the humidifier 309 to the patient connector 304 where it is released through the jet nozzle 410 (FIG. 4) into the tube 407 for delivery to the patient.

The advantages of the system depicted in FIGS. 3 and 4 over that depicted in FIGS. 1 and 2 include the allowance for the patient to breathe spontaneously from the gas supplied via humidifier 308, etc. while high frequency pulses of gas are delivered independently through the jet nozzle 410. In addition, gas from the humidifier 308, etc., may be entrained by the drag effects of jet nozzle 410 and less gas and, hence, less pressure is required to be delivered by the jet nozzle 410. In summary, the FIGS. 3 and 4 system, although more complicated, may provide better ventilation of the lungs.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. Apparatus for assisting a person's respiration by supplying gas pulses to the person's respiratory system where the frequency of the pulses is varied over a range which includes the resos pulses to the person's respiratory system where the frequency of the pulses is varied over a range which includes the resonant frequency of the person's respiratory system, said apparatus comprising means for producing a series of gas pressure pulses,
means for automatically varying the frequency of occurrence of the pulses to repetitively sweep over a selected range which includes the resonant frequency of the person's respiratory system, and
means for supplying the pulses to the person's respiratory system.

2. Apparatus as in claim 1 wherein said varying means includes means for periodically varying the frequency of the pulses over selectable ranges.

3. Apparatus as in claim 2 wherein said varying means includes means for selectively changing the periodicity of said frequency variation.

4. Apparatus as in claim 1 wherein said range is about 2 Hertz to 40 Hertz.

5. Apparatus as in claim 1 wherein said producing means comprises a high pressure source of gas, and inhale valve means coupled between said source of gas and said supplying means, and responsive to a first signal for closing to prevent the flow of gas from the source of gas to the supplying means, and to a second signal for opening to allow the flow of gas from the source to the supplying means, and wherein said varying means comprises means for alternately producing said first and second signals at a frequency which varies over the selected range, and for applying said signals to said inhale valve means.

6. Apparatus as in claim 5 wherein said signal producing means comprises a microprocessor.

7. Apparatus as in claim 5 further comprising heater means for warming the gas supplied by the high pressure source.

8. Apparatus as in claim 7 further comprising
control means for controlling the heat produced by said heater means to increase the heat when a temperature signal is below a certain level and to decrease the heat when the temperature signal is above the certain level,
temperature transducer means attached to the supplying means for producing a temperature signal indicative of the temperature of the gas pressure pulses, and
means for applying the temperature signal to the control means.

9. Apparatus as in claim 5 further comprising humidifier means for humidifying gas supplied by the high pressure source.

10. Apparatus as in claim 5 further comprising
pressure regulator means coupled between the high pressure source and the inhale valve means for controlling the pressure of the gas delivered to the inhale valve means by increasing the pressure when a pressure signal is below a certain level and by decreasing the pressure when the pressure signal is above the certain level, and
pressure transducer means coupled to the supplying means for producing a pressure signal representative of the pressure near the trachea of the patient.

11. Apparatus as in claim 5 wherein said producing means further includes exhale valve means coupled to said supplying means to allow escape of gas from said supplying means when the inhale valve means is closed, and to prevent the escape of gas from said supplying means when the inhale valve means is closed.

12. Apparatus as in claim 11 further comprising flow transducer means coupled to the exhale valve means for measuring the volume flow of gas flowing from the exhale valve means.

13. Apparatus as in claim 11 further comprising heater means for warming gas flowing from the supplying means.

14. Apparatus as in claim 5 further comprising
means for producing a second series of gas pressure pulses whose frequency is less than that of the first mentioned series, and
means for delivering the second series of pulses to said supplying means so that the pulses can be applied to the person's respiratory system.

15. Apparatus as in claim 14 wherein said second pulse series producing means comprises
a second inhale valve means coupled between said source of gas and said delivering means, and responsive to a third signal for closing to prevent the flow of gas therethrough and to a fourth signal for opening to allow the flow of gas therethrough, and
means for alternately producing said third and fourth signals at a predetermined frequency and for supplying the signals to said second inhale valve means.

16. Apparatus as in claim 15 wherein said third and fourth signal producing means comprises a microprocessor.

17. Apparatus as in claim 15 further comprising heater means for warming the gas which flows through the second inhale valve means.

18. Apparatus as in claim 17 further comprising
control means for controlling the heat produced by said heater means to increase the heat when a temperature signal is below a certain level and to decrease the heat when the temperature signal is above the certain level,
temperature transducer means attached to the supplying means for producing a temperature signal indicative of the temperature of the gas in the supplying means, and
means for applying the temperature signal to the control means.

19. Apparatus as in claim 15 further comprising humidifier means for humidifying the gas which flows through the second inhale valve means.

20. Apparatus as in claim 15 wherein the frequency of the second series of pulses is from about one per minute to 100 per minute.

21. Apparatus as in claim 15 wherein said supplying means includes
a manifold coupled to said second inhale valve means for receiving gas therefrom,
a tube coupled to the manifold for insertion into the mouth and throat of the person; said tube being coupled to the manifold to receive gas therefrom, and
a nozzle disposed to extend into the manifold to a point near or beyond the connection of the tube to the manifold, said nozzle being coupled to said first mentioned inhale valve means for receiving gas therefrom.

22. Apparatus as in claim 21 further including
exhale valve means coupled to said manifold and operable to open when said second valve means is closed to thereby allow the escape of gas from the manifold, and to close when said second valve means is opened to thereby prevent the escape of gas from the manifold.

23. A method of applying a series of gas pressure pulses to a person's respiratory system to assist ventilation and respiration of the person, said method comprising the steps of producing a series of gas pressure pulses,
automatically varying the frequency of occurrence of the pulses to repetitively sweep over a selected range of frequencies which includes the natural frequency of the person's respiratory system, and
supplying the pulses to the person's respiratory system.

24. A method as in claim 23 wherein said varying step comprises varying the frequency of gas pressure pulses over a range of from about 2 Hertz to 40 Hertz.

25. A method as in claim 23 further including the step of selectively changing the periodicity of frequency variation.

26. A method as in claim 23 further comprising the step of warming the gas before supplying it to the person's respiratory system.

27. A method as in claim 23 further comprising the step of humidifying the gas before supplying it to the person's respiratory system.

28. A method as in claim 23 further comprising the steps of
detecting the pressure of gas introduced to the patient's respiratory system, and
increasing the pressure of the gas pulses if the pressure detected is below some predetermined level and reducing the pressure of the gas pulses if the pressure detected is above the predetermined level.

29. A method as in claim 23 further comprising the steps of
producing a second series of gas pressure pulses which have a lower frequency than that of the first mentioned series, and
supplying the second series of pulses to the person's respiratory system in conjunction with the first mentioned series.

30. A method as in claim 29 wherein the frequency of the second series of pulses is from about one to 100 pulses per minute.

* * * * *

UNITED STATES PATENT AND TRADEMARK OFFICE
CERTIFICATE OF CORRECTION

PATENT NO. : 4,481,944
DATED : Nov. 13, 1984
INVENTOR(S) : J. Bert Bunnell

It is certified that error appears in the above-identified patent and that said Letters Patent are hereby corrected as shown below:

Claim 1, lines 54-56, delete "the resos pulses to the person respiratory system where the frequency of the pulses is varied over a range which includes"

Signed and Sealed this

Seventeenth Day of December 1985

[SEAL]

Attest:

DONALD J. QUIGG

Attesting Officer

Commissioner of Patents and Trademarks